US005507790A

United States Patent [19]
Weiss

[11] Patent Number: 5,507,790
[45] Date of Patent: Apr. 16, 1996

[54] METHOD OF NON-INVASIVE REDUCTION OF HUMAN SITE-SPECIFIC SUBCUTANEOUS FAT TISSUE DEPOSITS BY ACCELERATED LIPOLYSIS METABOLISM

[76] Inventor: William V. Weiss, 193 Hudson Dr., Toronto, Ontario, Canada, M4T 2L7

[21] Appl. No.: 215,743

[22] Filed: Mar. 21, 1994

[51] Int. Cl.⁶ ........................................ A61F 7/00
[52] U.S. Cl. .............................. 607/100; 600/2; 128/897
[58] Field of Search ..................... 600/2, 10; 601/2; 607/96–106; 128/898

[56] References Cited

U.S. PATENT DOCUMENTS

| | | | |
|---|---|---|---|
| 4,525,359 | 6/1985 | Greenway, III et al. | 514/653 |
| 4,588,724 | 5/1988 | Greenway, III et al. | 514/250 |
| 5,143,063 | 9/1992 | Fellner | 128/399 |

OTHER PUBLICATIONS

"Deep Local Hyperthermia For Cancer Therapy: External Electromagnetic and Ultrasound Techniques", A. Y. Cheung et al., Cancer Research, vol. 44, Oct. 1984, pp. 4736–4744.
"Principles of ultrasound used for generating localized hyperthermia", J. W. Hunt, in: Introduction to Practical Aspects of Clinical Hyperthermia, Field S. B. & Hand J. W., Publ., Taylor & Francis, London, 1990.
"Mechanisms Underlying Regional Differences in Lipolysis in Human Adipose Tissue", Wahrenberg et al., J. Clin. Invest., vol. 84, Aug. 1989, pp. 458–467.
"Adrenergic receptor function in fat cells", Aner, P., American Journal of Clinical Nutrition, 1992; 55:228S–36S.
J. C. Bamber, Attenuation and absorption. In: C. R. Hill (ed) Physical Principles of Medical Ultrasonics, Ch. 4, Ellis Horwood, Chichester, England, 1986.
"Computationally efficient algorithms for control of ultrasound phased array hyperthermia applicators based on a pseudoinverse method", E. F. Ebbini, et al., IEEE Trans. Ultrason. Ferroelec. Freq. Contr., 37, 6, pp. 274–276, 1990.
"Sound field calculations for rectangular sources", K. B. Ocheltree, et al., IEEE Trans. Ultrason. Ferroelec. Freq. Contr., 36, 2, pp. 242–248, 1989.
"Tumour Eradication by Radiofrequency Therapy Response in 21 Patients", H. H. LeVeen, et al., JAMA, vol. 235, No. 20, pp. 2198–2200, 1976.
"The effect of ultrasound on in vitro liberation and in vivo penetration of benzyl nicotinate", D. Hofmann, et al., Journal of Controlled Release, vol. 27, 1993, pp. 185–192.
"Regional Fat Loss from the Thigh in Obese Women after Adrenergic Modulation", F. L. Greenway, et al., vol. 9, Clinical Therapeutics, No. 6, 1987, pp. 663–669.
"Field Conjugate Acoustic Lenses for Ultrasound Hyperthermia", R. J. Lalonde, et al., IEEE Trans. Ultrason. Ferroelec. Freq. Contr., 40, 5, pp. 592–602.
"Equipment For Local Hyperthermia Therapy of Cancer", C. F. Babbs, et al., Medical Instrumentation, vol. 16, No. 5, Sep.–Oct., 1982 at 245–248.
"Sonophoresis. I. The Use of High–Frequency Ultrasound to Enhance Transdermal Drug Delivery", D. Bommannan, et al., Pharmaceutical Research, vol. 9, No. 4, 1992.

Primary Examiner—Angela D. Sykes
Assistant Examiner—Robert L. Neisser, Jr.
Attorney, Agent, or Firm—Jeffrey T. Imai; Anre I. Fors; D. Doak Horne

[57] ABSTRACT

Electromedical apparatus is employed together with local topically applied drugs and general medical management program to non-invasively, non-traumatically, reduce in volume without fat cell death, specific local accumulations of stored triacylglyceride by localizing (e.g., focusing) radiant energy and/or localized lipolysis augmentation methods, thereby accelerating local fat tissue lipolysis reaction rates. The radiant energy includes, localized radio frequency, microwave or ultrasound energy, which impinges upon the fat cells to be reduced in volume but not killed or eliminated. Fat cell size reduction occurs through the mechanism of accelerated lipolysis rate which is a function of local cell temperature elevation and local fat cell lipolysis rate augmentation by local lipolytic drug delivery.

20 Claims, 3 Drawing Sheets

5,507,790

METHOD OF NON-INVASIVE REDUCTION OF HUMAN SITE-SPECIFIC SUBCUTANEOUS FAT TISSUE DEPOSITS BY ACCELERATED LIPOLYSIS METABOLISM

FIELD OF THE INVENTION

This invention relates to a method and apparatus for non-invasive, non-traumatic shaping and contouring of a human body by external means. In particular, this invention relates to the integrated employment of localized or focused radiant energy in conjunction with specific general medical management protocols and more specific "directed" localized therapeutic medical topical lipolysis augmentation techniques to non-invasively and non-destructively downsize underlying subcutaneous fat tissue volume and thereby modify contour/shape local target subcutaneous adipose tissues by accelerating local fat tissue metabolism.

BACKGROUND OF THE INVENTION

ANATOMY/MICROANATOMY/HISTOLOGY

Adipose tissue "fat" is formed by aggregations of fat cells (adipocytes) containing stored fat (lipid) in the form of single droplets of triacylglycerol (triglyceride). Fat tissue is comprised of clusters of adipocytes ranging from small fat cells (SFC) to large mature fat cells (MFC). They are typically spherical but may assume polyhedral shapes because of mutual deformation. A single fat cell is 95% fat by volume. The cell nucleus is displaced to one side by the accumulated lipid and the cytoplasm is reduced to a thin rim. Each individual fat cell has large numbers of hormone and other receptors in the cell wall.

There are many different types of receptors, including, alpha and beta adrenergic receptors, and insulin receptors. Other types of receptor include: sex hormone receptors, glucocorticosteroid receptors, and other classes of receptor. A single adipocyte (fat cell) may have as many as 5,000 to 10,000 receptors. The various receptors are made of proteins with complex three-dimensional conformations. Each receptor is specialized to recognize single, or occasionally several types of chemical or hormonal signals.

Each fat cell is surrounded by delicate reticular fibers. In the angular spaces between the cells are capillaries and nerve supplies that form a loose plexus throughout the tissue. Adipose tissue is subdivided into small lobules by connective tissue septa. This compartmentalization, visible with the naked eye, is most obvious in regions where the fat is subjected to pressure and has a cushioning or shock-absorbing effect. In other regions the connective tissue septa are thinner and the lobular organization of the tissue is less apparent.

Adipose tissue is distributed in the subcutaneous tissue but exhibits regional differences influenced by genes, age, sex, activity levels and eating habits. Adipose tissue collectively constitutes a large diffuse "organ" that is metabolically very active; it is primarily engaged in the uptake, synthesis, storage (accretion), and mobilization (release/depletion) of neutral lipid or fat. As a result of release, the caloric content of the lipid stored in the fat can be made available as heat or as energy to cells in other parts of the body. At body temperature, the lipid in adipocytes is present as liquid oil. It consists of triacylglycerol, each made up of three molecules of fatty acid esterified to glycerol.

Infants and young children have a continuous subcutaneous layer of fat. The panniculous adiposus is generally a uniform thickness over the entire body. As the young child grows to an adult, the fat layer thins out in some regions of the body but persists and grows thicker in certain sites of predilection. These sites differ between sexes and are largely responsible for the characteristic contour differences in male and female body form.

In the male, the principal areas of predilection are the neck and the region overlying the seventh cervical vertebra, the subcutaneous area overlying the deltoid and triceps, the lumbosacral region, and the buttocks.

In the female, subcutaneous fat is most abundant in the anterior neck, the breasts, the buttocks, the epitrochanteric region, and the anterior aspect of the thigh. Few blood vessels pass through subcutaneous fat into the overlying skin, which receives its nutrients through a subdermal plexus of blood vessels which run above the fatty layer.

In addition to the superficial subcutaneous fat deposits of varying thickness covering the body, there are extensive "deep" internal abdominal (visceral) accumulations in both sexes in the omentum, mesenteries, and retroperitoneal areas. All of these areas, to varying degrees, readily give up, or "release" by the process of lipolysis, their stored lipid during fasting.

Obesity is defined as an increase in the mass of adipose tissue. Humans accumulate excess body form, shape, or "contour-determining" subcutaneous adipose deposits in the body when energy intake derived from food exceeds daily energy needs. This may be accomplished by an increase in fat cell size or fat cell number or an increase in both fat cell size and number. Once obesity is established, weight reduction is accomplished by a decrease in fat cell size or volume and the number of fat cells remains relatively unchanged.

The diversity of human shape or contour seen in differing individual bodily fat accumulations depends on a complex combination of factors such as, age, sex, lifestyle, genetic and hormonal influences.

PHYSIOLOGY/BIOCHEMISTRY

Lipolysis is the physiological mechanism by which adipose tissues "mobilize" or release the stored fat energy to make it available as energy for metabolic activities. Free Fatty Acids (FFA) are the specific molecular energy substrate of lipolysis, and are used by many body tissues as an alternate energy substrate to glucose (blood sugar). Muscles in particular utilize very large amounts of FFA in a regular fashion depending on an individuals diet and exercise behaviour. Muscles throughout the body have an enormous capacity to utilize FFA released by the lipolytic process.

Research has firmly established that hormones, specifically catecholamines (epinephrine and non-epinephrine), are the principal naturally occurring lipolytic hormones that initiate human lipolytic processes via adipocyte adrenergic receptors. On the other hand, numerous endogenous antilipolytic substances can inhibit lipolysis in human fat cells through distinct receptors. These include insulin, prostaglandins, adenosine, and insulin-like growth factors. Since all of these substances (except insulin) are produced locally in adipose tissues, it is possible that paracrine regulation is of great importance for lipolysis control. However, it is the net effect of both these antilipolytic substances and lipolytic catecholamines (both stimulatory and inhibitory) on adipocyte adrenergic receptors (both alpha and beta) that signal the lipolytic machinery of these cells to decrease or increase lipolysis.

Recent research has clearly established that the mix of human adipocyte lipolytic receptor populations varies considerably in different anatomical locations ("Mechanisms Underlying Regional Differences in Lipolysis in Human Adipose Tissue", Wahrenberg et al., *J. Clin. Invest.*, Vol. 84, Aug. 1989, pp. 458–467.) in the body. More specifically fat cells in differing anatomical sites are not identical and do not have identical sets of lipolytic (adrenergic), sex, and other hormone receptors.

In men and women, the major contributing mechanism is a regional difference in the expression of beta adrenoceptor. The order of magnitude for the number of beta receptors in vitro and in vivo is: omental>subcutaneous abdominal>subcutaneous peripheral.

In women, there are also regional variations in $alpha_2$-receptor activity within the subcutaneous fat depot. There is a higher $alpha_2$-receptor affinity in peripheral than in abdominal subcutaneous fat cells, which may explain why the regional variation in catecholamine-induced lipolysis within the subcutaneous adipose tissue is more pronounced in women than in men ("Adrenergic receptor function in fat cells", Arner, P., *American Journal of Clinical Nutrition*, 1992;55:228S–36S). Thus, for example, female thigh fat cells may have differing collections of both adrenergic and sex hormone receptors than the adipocytes of the abdominal subcutaneous fat cells, or additionally sex hormones modulate beta-adrenoceptor numbers or sensitivity.

There is growing evidence that other hormones such as glucocorticosteroids also play a role in the lipolytic process, and particularly in the deep intra-abdominal visceral fat of the omentum. Recent evidence indicates that visceral fat cells have larger numbers of glucocorticosteroid receptors than in other subcutaneous fat tissues. All these factors account for the considerable variation in human body subcutaneous and other fat deposit distribution, and for the differing responses of these fat accumulations to exercise, diet, and stress in males and females.

Regardless of sex, it is becoming clearer that a predominant abdominal fat distribution, including the very important internal visceral fat deposits of the omentum, is a greater risk factor for heart disease, diabetes, and other metabolic disorders than other fat distributions, ie: the "apple" shape (bad) as opposed to the "pear" (good) body shape (i.e. waist circumference to hip circumference ratio>1).

Most fat tissue accumulations result from lipids, fat primarily from food, in the circulation becoming stored into individual fat cells (adipocytes) as droplets of triacylglycerol (commonly called "triglycerol") or fat, which is a glycerol molecule plus 3 fatty acid molecules. When the reaction is in the direction of fat cell lipid uptake or storage, the reaction is initiated by the hormone insulin, and catalyzed by the enzyme lipoprotein lipase (LPL) and the fat cells enlarge/ swell. When the reaction is in the opposite direction of lipolysis or release, the fat cells shrink in size, as stored adipocyte triglyceride is converted to glycerol and free fatty acids. The FFA's move out of the fat cells into the circulation and are utilized as an energy substrate by the body. The glycerol is returned to the liver for resynthesis of glycogen.

Lipolysis is a hormone initiated and enzyme-catalyzed reaction. Adipocyte hormone-sensitive lipase (HSL-not to be confused with lipoprotein lipase or LPL) is the key rate-limiting enzyme of this fat-mobilizing or lipolytic process. The hormone sensitive lipase enzyme activity is triggered primarily by increases in local catecholamines.

All enzyme-mediated biological reaction rates, including those of adipose tissue (lipolysis), are temperature sensitive. Temperatures less than 36° C. slow reaction rates and temperatures above 36° C. raise reaction rates in a more or less linear fashion until killing temperatures exceeding 43° C. are maintained for a sufficient duration to stop all biological enzyme reactions by protein denaturation.

Human adipose tissue storage accumulations in various anatomical locations swell and shrink in a dynamic and regular way depending on genetic predisposition, individual life styles, and other incompletely understood factors. Adipose tissues, as a result of a complex interplay of regulatory factors controlling their metabolic behaviour, currently should be viewed more as a "smart cellular compartment" containing stored energy and possibly other endocrine (hormonal) products which are responsive to many physiological signals rather than simply a large passive container of stored fat. Thus, contrary to the general perception, the total adipose tissue of obese, as well as normal weight, individuals is a dynamic organ in a constant state of flux or "turn-over". The resulting change in volume of such fat tissue varies as a function of the current state of individual overall energy balance, hormone and neural mediators. Such volume changes are reflected in the various local body fat deposits in complex ways.

It is well established that obese individuals who are able to lose large amounts of weight do so as a result of gradually reducing the volume of stored fat at the individual fat cell level (by as much as several orders of magnitude i.e. 100 to 1,000 times) by the process of lipolysis. The aesthetic problem for most individuals who achieve modest or even significant degrees of weight loss, is that the adipose tissue volume reduction is often not lost from the specific anatomical sites they desire (e.g. tummy, buttock, thigh), but occurs rather unpredictably from all anatomical areas.

TRANSDERMAL DRUG DELIVERY/TARGETING, PHONOPHORESIS, IONTOPHORESIS

Transdermal drug targeting is a rapidly developing therapeutic modality for delivering externally applied medications through the skin to deeper skin layers and/or systemic circulation. The most popular current devices for such drug delivery employ patch formulations which contain a small reservoir of medication which when the patch is applied to the skin delivers the drug through the skin to the circulation at a very predictable and controlled rate and dose.

For smoking cessation, there are nicotine patches; for hormone replacement therapy in female menopause, there are estrogen patches. For motion sickness, there are dramamine patches. All these surface applied patches deliver medication only a few millimeters to the subdermal plexus of tiny capillary blood vessels and hence to the wider systemic circulation.

Recently, a patch containing medications for a slightly deeper skin layer have emerged for certain psoriatic (psoriasis) skin lesions. In order to influence surface-applied medication to penetrate deeper than the dermis, such as into the subcutaneous fatty tissue layers and deeper, additional directive or motive measures must be used with surface applied compounds.

Alternatively, simple topical drug formulations (creams etc.) can be used. However, such topical formulations tend only to affect the outermost layers of the skin, rarely penetrating to the subdermal vascular plexus. No effective commercial lipolytic topical formulations are currently available.

However, many existing and approved pharmaceutical agents with known and proven adipocyte alpha$_2$ and beta$_2$ adrenergic receptor lipolytic effects are available. When formulated in a cream, ointment, or gel base and applied to the skin surface, the active drugs diffuse through the outer epidermal and dermal layers into the subcutaneous fatty tissues where the lipolysis-augmenting effect takes place.

Phonophoresis, for example, could be employed as a "motive force" or method of delivering topically applied medication(s) into the subdermal or subcutaneous tissues by the use of ultrasonic radiation pressure to "drive" the medication/s on the surface deeper into the underlying tissues. This modality has been increasingly employed by physical therapists for the noninvasive (i.e. no injection) treatment of musculoskeletal disorders. Traditionally, hydrocortisone has been the medication applied most commonly in phonophoresis, but the topical anaesthetic agent lidocaine has also been used to give pain relief without injection. Phonophoresis tissue penetration depth is dependent on a combination of medication molecular size, hydrophillic or lipophilic character, skin subcutaneous and deeper tissue character, ultrasonic frequency, continuous or intermittent/pulse mode operation, power and other variables.

Iontophoresis is a related technique for targeting surface/electrode applied medications into very superficial tissues. Iontophoresis utilizes electro-motility forces by the application of a potential difference (voltage) across skin electrodes. This method moves medications only superficially (3–4 mm) into the tissues, but achieves higher superficial tissue-drug concentrations than phonophoresis and is used by physical therapists for treating ligament and tendon injuries.

CANCER HYPERTHERMIA

Historically the primary use of hyperthermia applied to medical problems has been in the cancer treatment or oncology field. All prior hyperthermia art has been designed as an adjunct to enhance tumour killing or as treatment in conjunction with radiotherapy or chemotherapy. Only recently has hyperthermia been employed to kill relatively normal tissues in applications such as the destructive heating of portions of the prostate gland (Transurethral Microwave Thermotherapy or TUMT) in patients with benign prostatic hypertrophy (BPH).

Electromedical methods and apparatus have been used in the past for various surgical and therapeutic procedures. Historically, each of these systems has recognized the need to avoid damage to adipose or other tissue surrounding the tumour tissue desired to be destroyed.

Of all the different tissues in the human body, adipose tissue is one of the most "transparent" or least absorbing of ultrasonic energy, with bone, tendon, skin, muscle, connective tissue and organs being much more disposed to absorb ultrasonic energy (J. C. Bamber, Attenuation and absorption. In: C. R. Hill (ed) Physical Principles of Medical Ultrasonics, Ch. 4. Ellis Horwood, Chichester, England, 1986). Alternatively, other types of radiation, ie. microwave or radio frequency (RF), have different tissue absorption characteristics than ultrasound and can be absorbed preferentially by fatty tissues as is well known in capacitive RF hyperthermia therapy.

There has been a recognition that during hyperthermia cancer therapy any other normal tissue should not be heated inadvertently during treatment, and a further recognition that adipose/other tissue, being more effectively blood-cooled than tumour tissue, is inherently unlikely to inadvertently receive a damaging energy dosage during hyperthermia treatment by means of the prior systems intended for treatment of tumours or the like.

OTHER NON-CANCER TISSUE HYPERTHERMIA APPLICATIONS

In U.S. Pat. No. 5,143,063, Sep. 1, 1992, Fellner describes a very general destructive method of "removing" normal body fatty tissues by heating the body fat tissues to cellular destructive or killing hyperthermic temperatures (in excess of 43° C. for at least 30–40 minutes). The hyperthermic temperatures destroy the target tissues and leave the body to remove the dead cellular and other debris.

The Fellner methodology, while hypothetically describing the possible reduction of fat deposits, is unlikely ever to receive widespread approval by the medical community. The Fellner method takes an otherwise normal, obese patient, and in the process of applying this fat tissue killing method, traumatizes the patient's fat tissues, inducing pain and making the patient sick as the body attempts to absorb an undefined volume of potentially toxic dead tissue debris, cellular and fat breakdown byproducts.

The amount of fat tissue volume required to be destroyed by Fellner to achieve cosmetic results (approximately 4000+ cc of tissue volume) would generate intense pain in the patient. In addition, very large and potentially toxic amounts of fat breakdown debris which would be loaded on the patient's internal waste management system.

SURGICALLY-ASSISTED LIPOSUCTION

Currently, the only method in regular medical use for the removal of undesirable deposits of fat from the body is the procedure termed surgical-assisted liposuction or "liposuction". In surgical liposuction practice, the surgeon employs different sized special fat suction cannulas with external vacuum hose attachments to remove or "suck out" selected volumes of subcutaneous fat from the patient at planned local anatomical sites of aesthetically "offending" body contour. It is not uncommon during such cosmetic procedures to "suck out" fat, blood, and associated tissue fluids in volumes of 2000–4000 cc. In extreme cases, as much as 5500 cc of fat and other interstitial tissue is suctioned away in such procedures.

Surgical-assisted liposuction procedures are traumatic, destructive, and invasive surgical methods for reducing excessive adipose tissue accumulations from the body. Liposuction has many undesirable side effects and risks, with a worst case scenario being the death of a patient (fat embolism, etc.).

Due to the invasive, destructive and painful nature, the liposuction procedure requires a general anesthesia to be administered with the attendant risks and many other undesirable associated side-effects.

SUMMARY OF THE INVENTION

The disadvantages of the prior art may be overcome by providing a method of reducing the volume of regional or site-specific accumulations of subcutaneous adipose tissue noninvasively, gradually, without tissue damage. In particular, this invention relates to a safe and specific method of fat volume reduction/downsizing by a non-destructive metabolic acceleration of normal fatty tissue lipolytic activity without killing or traumatizing these, or associated tissues.

It is desirable to provide a method which applies a new combination of electromedical technologies and medical therapeutic measures.

It is further desirable to provide a system for modulating or altering nondestructively the metabolic responses of adipose tissues in desired locations (chin, arm, leg, trunk, abdomen, buttock, thigh, etc.), to accelerate lipolysis, thereby resulting in body shape/contour change.

It is further desirable to provide a method which utilizes radiation-induced "sub-hyperthermia" (temperatures lower than the customary hyperthermic cell-killing temperatures) in conjunction with site-specific lipolytic augmentation drug targeting techniques to accelerate normal fat tissue lipolytic rates, thereby reducing adipose tissue volume.

It is still further desirable to provide a method of focusing tissue heating radiation to the target fat tissues.

It is still further desirable to provide a method of generating uniform, focused and "shaped" ultrasonic fields to permit the external modification of target fat tissue metabolism in a controlled and predictable fashion by the creation of very specific geometric temperature fields in the local fat tissue under treatment. By the creation of such exact temperature zones or fields, the precise anatomical location, depth, size and shape of the subcutaneous fat accumulation can be selected.

According to one aspect of the present invention, there is provided an electromedical method for noninvasively, nondestructively and without tissue trauma, accelerating lipolysis of subcutaneous adipose ("fat") tissue. The method comprises the preliminary steps of:

- assessing overall health, fitness, and suitability of a subject for any local or general medical intervention;
- performing baseline medical, laboratory, biometric, and contour measurements prior to treatment;
- determining whether to utilize topical lipolytic augmentation agents in conjunction with other radiant energy modalities in a particular subject;
- determining an overall treatment program and schedule which includes: the number of encounters necessary to achieve satisfactory site-specific body contour modification by the reduction of local subcutaneous adipose tissue volume, and a medical management program which achieves a modest catabolic metabolic or negative caloric state;
- determining the specific geometric pattern of application of local site-specific adipose tissue volume reduction to optimize the treatment program utilizing computer simulation technique. The method of reducing adipose cell volume in a human subject by non-invasively, non-destructively, and atraumatically increasing lipolysis at specific accumulations of subcutaneous adipose tissue comprises the steps of:
- determining a desired work site in the subject's subcutaneous adipose tissue layer containing healthy adipose cells to be reduced in volume;
- focusing radiant energy on the work site to raise the temperature thereof to range of about 40.0° to 41.5° C., but less than 43° C.; and
- maintaining the radiant energy focused on the work site to increase lipolysis rates thereof sufficiently to cause release of FFA, thereby reducing the volume of the adipose cells.

According to another aspect of the invention there is provided a method of a combination of localizing or non-focusing radiant energy, and/or directed topically applied lipolytic augmentation drugs, together with specific medical management protocols to reduce fat tissue volume without tissue destruction at desired local sites of fat accumulation.

BRIEF DESCRIPTION OF THE DRAWINGS

The above and other features and advantages of the invention will become more clear from the following detailed description of an illustrative embodiment thereof, presented herein below in conjunction with the accompanying drawings, in which.

DETAILED DESCRIPTION OF THE INVENTION

All biological tissues contain enzymes that have activities which are particularly sensitive to temperature. In general, biological activity increases 2–3 times for every 10° C. rise in temperature. The use of controlled and focused heat alone or in combination with lipolytic augmentation drugs increases lipolytic rates significantly, resulting in mobilization or depletion of stored fat by the process of lipolysis, and thereby resulting in local fat volume reduction under the proper medical management.

Medical management can include simple measures to maintain the subject in a slightly "catabolic" or "negative" caloric state. Such a desired catabolic state can be achieved in most individuals by very modest reductions in the amount of their daily consumption of food or by changes in the type of food (i.e lower percent of fat-containing foods), accompanied by a slight increase in physical activity levels. As little as a 100 calories less per day reduction of food, and as little as a 100 calories increase of energy expended may be satisfactory to obtain desired results. Given this catabolic state, the muscles of the human body will utilize as an energy substrate, all fatty acids released or mobilized by the proposed lipolytic acceleration method and result in local/regional and thus site-specific subcutaneous fat volume reduction.

Figure 1:
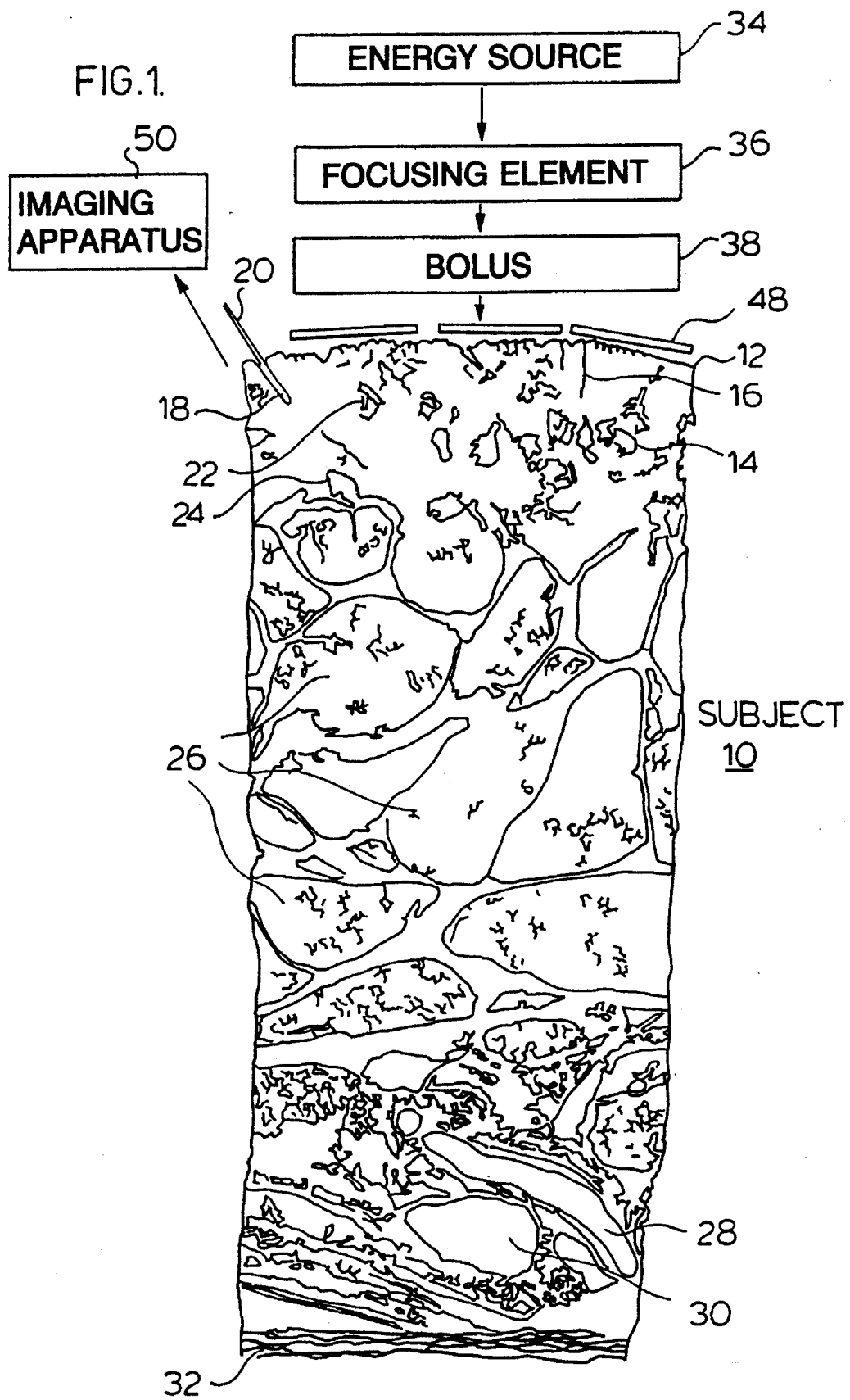
FIG. 1 is a schematic diagram of the present invention and depicting in cross-section through the human thigh perpendicular to the surface of the skin and including from the surface down: the human epidermis, dermis, subcutaneous fat tissue, and muscle.

Referring now to FIG. 1, there is shown a system for the non-invasive, non-destructive, atraumatic, controlled reduction in volume of subcutaneous adipose ("fat") tissue. The skin about a human subject 10 has an epidermis (outer) layer 12 disposed over a dermis layer 14. Passing through the epidermis 12 into the dermis 14 are sweat gland ducts 16 and hair follicles 18 through which hair 20 protrudes. Embedded in the dermis are sebaceous glands 22 and sweat glands 24. Immediately beneath the dermis is the subdermal plexus of small blood vessels (not shown for clarity). Disposed beneath the dermis is a layer of subcutaneous adipose tissue 26, which is of widely varying thickness in different individuals (from less than 1 cm to in excess of 10 cm). Beneath the fat layer are such structures as blood vessels 28, lymphatic vessels 30 and muscle layers 32.

As noted above, the subcutaneous adipose tissue layer 26 may be thin (1 cm or less) or within reasonable bounds in subjects of slight or moderate build. In some people, however, the subcutaneous adipose layer 26 becomes very thick (exceeding 10–15 cm) in morbid obesity.

In accordance with the present invention, an ultrasonic transducer or energy source 34 supplies radiant energy of a specific frequency to a focusing element 36. The transducer 34 and the focusing element 36 are interfaced with the human subject 10 through a temperature controlled water bolus 38, which protects the skin and top layer of epidermis 12 and dermis 14 from damaging and painful effects of too much heating/energy absorption that skin absorbs.

The water bolus 38 can hold the top layers of skin and underlying dermis and epidermis at "body" temperatures or lower (28°–35° C.) as desired by the operator in accordance with procedures well known to those skilled in the art. A temperature controller and water circulation system external to the water bolus 38 is used to maintained the desired surface temperature. Preferably, the water circulating through the water bolus 38 is deionized water "degassed" by an external system. Degassing prevents gas bubbles from absorbing ultrasonic radiation.

The focusing element 36 directs or focuses the radiant energy generated by the transducer 34 to a particular zone of impingement in the subcutaneous adipose tissue layer 26.

Figure 2:
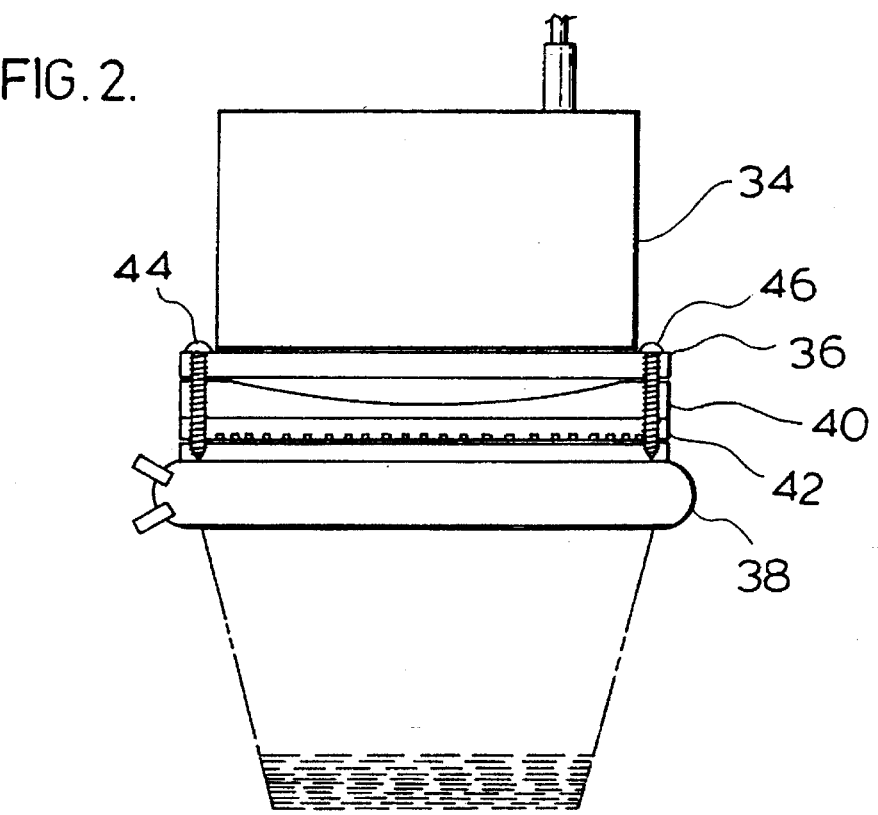
FIG. 2 is a cross-sectional view of a flat planar ultrasonic transducer interfaced to a lens array including a simple concave lens and a field-conjugate acoustic lens.

In one embodiment of the present invention as illustrated in FIG. 2, the focusing element 36 comprises both a simple concave lens 40 and a field-conjugate acoustic lens 42. The two lenses are mounted onto the housing of transducer 34 in any convenient manner to affix the lenses in place. The lenses 40 and 42 are sandwiched between a mounting plate and the housing of transducer 34 using screws 44 and 46. The order of the two lenses 40 and 42 is not critical as a reverse order, i.e. lens 42 adjacent the trasnducer 34 will produce the same result.

The concave lens 40 has a concave surface on the radiation wave-incident side and a flat planar surface configuration on the exit face. The planar surface is placed against a flat planar surface of the conjugate lens 40 on its radiation wave-incident side and a complex machined exit face. Such focusing elements are more fully described in a text entitled *Ultrasonics, Theory and Application* by G. L. Gooberman. The use of such a focusing lens for ultrasound energy, with a planar wave-receiving face and concave wave-exiting face, is described in "Deep Local Hyperthermia For Cancer Therapy: Extreme Electromagnetic and Ultrasound Techniques", A. Y. Cheung and A. Neyzari, Cancer Research, Vol. 44, October 1984, pp. 4736–4744. Ultrasonic energy may be focused by a concave ceramic generator, or by employing a system of reflectors.

Additionally, in this embodiment the specific lens design physics of the field conjugate acoustic lens 42 is called "field-conjugate acoustic lens technology" (see "Principles of ultrasound used for generating localized hyperthermia", Hunt, J. W. in: Introduction to Practical Aspects of Clinical Hyperthermia, Field S. B. & Hand J. W., Publ., Taylor & Francis, London, 1990; J. Hunt et al., Field conjugate Acoustic Lens/Hyperthermia, personal communication, 1993; Ebbini, E. F., et al., "Computationally efficient algorithms for control of ultrasound phased array hyperthermia applicators based on a pseudoinverse method", IEEE Trans. Ultrason. Ferroelec. Freq. Contr., 37, 6, pp. 274–276, 1990; Ocheltree, K. B., et al., "Sound field calculations for rectangular sources", IEEE Trans. Ultrason. Ferroelec. Freq. Contr., 36, 2, pp. 242–248, 1989).

Utilizing algorithms and known fabrication methods, an acoustic lens 42 can be designed to have a large range of temperature field patterns at certain tissue depths. Additionally, combinations of simple traditional concave ultrasonic lenses and conjugate lenses can be employed. For example, a cylindrical shaped uniform temperature field of 41° C. with a diameter 6 cm and thickness of 2 cm, at a work site depth of exactly 1.5 cm can be achieved by a lens. Alternatively, for example, a spherical temperature field of 41.5° C., having a diameter of 3 cm, and a working depth of 4 cm can be achieved by a lens.

As is apparent, the shape of the concave surface and/or the more complex conjugate lens will determine the depth at which the energy penetrates and focuses in the desired work zone. A different lens might be required for application of the present invention to each anatomical area, such as thighs, abdomen, arms etc.

The ultrasonic energy emitted from the transducer 34 may be of any kind which is capable of being localized by a focusing element 36, such that the emitted energy impinges at a variable, controlled focal location within the adipose layer 26. In the preferred embodiment, ultrasound energy is used. However, the energy source or transducer 34 might equally transmit radio frequency energy, microwave energy or the like. Associated with the use of the above modalities are several physical processes, including radiant, capacitive, inductive, and resistive (ohmic) heating.

In the first embodiment, ultrasound energy is applied through the temperature controlled water bolus 38. Additionally, the frequency of the ultrasound energy source can "sweep" between several frequency values when used with conjugate lenses having several temperature field patterns designed-in to their operating frequency range. This provides for flexibility in creating deeper controlled temperature fields as desired. Additionally, the ultrasonic field can operate continuously or in an intermittent pulse mode as desired.

The temperature in the temperature zone may be monitored with temperature sensing devices, either directly or indirectly to confirm that predictive computer simulation temperatures no greater than 41.5°–42° C. are in effect in order to prevent cell injury or death.

The temperature and the frequency of the ultrasound energy determine the penetration depth. The lower the frequency, the deeper the ultrasound energy will penetrate. By increasing or decreasing the skin temperature, the depth of the sonically heated tissue is shifted. By controlling these two factors, a specific work zone can be targeted.

Target fat tissue metabolic activity can be increased by the application of known topical lipolytic augmentation agents 48. The controlled application of radiant energy to heat the target tissue in combination with the lipolytic augmentation agents 48 increases lipolysis rates in adipose tissue. Such topically applied lipolysis augmentation agents can include, singularly or in various combinations: methyl xanthines such as theophylline, aminophylline, caffeine; pentoxifylline; beta-1 adrenergic agonists (stimulators) including, but not limited to: forskolin, norepinephrine, epinephrine, isoproteranol; specific beta-3 agonists (stimulators) including but limited to: fenoterol, clenbuterol; alpha-2 adrenergic inhibitors (antagonists) including but not limited to: yohimbine, rauwolscine, oxymetazoline, piperoxane, phentolamine, dihydroergotamine, idazoxin; adenosine inhibitors; calmodulin agonists; thyroid hormones including but limited to: T3/triiodothyronine and T4/tetraiodothyronine; sex hormones including but not limited to methyltestosterone; prostaglandin inhibitors including but not limited to aspirin (ASA), non-steroidal anti-inflammatory drugs (NSAID's), and finasteride, tamoxifen.

One skilled in this art is aware that the heating of the work zone should be only to an effective temperature and for an effective duration, and should not exceed an amount of heating that will damage or kill tissue at the work zone or the surrounding tissue. The key to this method is to apply energy to the work zone sufficient to raise this site to a temperature of about 40°–41.5° C., yet not exceed 42° C., thereby accelerating fat lipolysis without killing the fat cells or adipocytes.

The skilled person is also aware that no single specific combination of heating temperature, induced tissue temperature field pattern, and duration is appropriate for volume reduction of adipose tissue in all subjects. Rather, these parameters will vary with the particular physiology of the individual subject, including such factors as body weight and subcutaneous fat distribution pattern, health, age, sex, exercise regimen, general medical health, associated medical management program, the utilization of lipolytic augmentation agents, and other factors.

Optionally, an imaging apparatus 50 may be employed to view and monitor the adipose tissue modification/reduction process as it proceeds over the entire course of the treatment program. Imaging apparatus, such as, diagnostic ultrasound, thermography, CT, and MRI, digitized 3 dimensional laser contour scanning, "time-of-flight" laser tomography and the like, permit quantitative measurement and calculation of fat tissue reduction and/or intended to be reduced. Complete automated area/volume analysis can identify the location of a work zone to rapidly and progressively reduce adipose tissue volume.

The exact treatment program for any individual patient depends on the degree of adiposity, local contour concerns, overall medical condition (no contraindications to shape modification/reduction), and ultimate compliance with total medical protocols (diet, exercise, topical lipolytic augmentation and other tissue lipolytic augmentation targeting).

Figure 3:
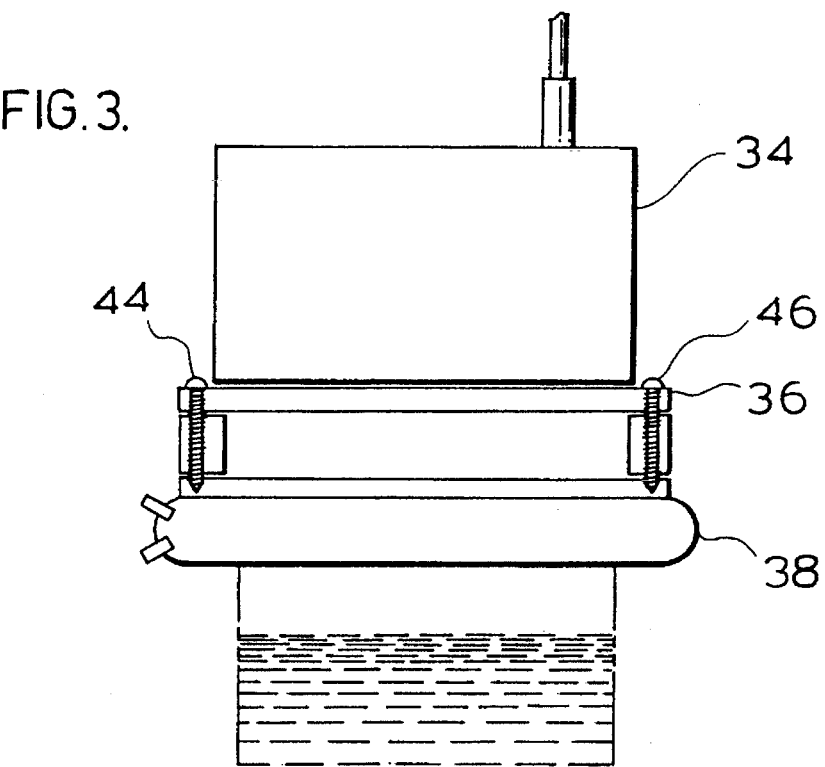
FIG. 3 is a cross-sectional view of a flat planar ultrasound energy source identical to FIG. 2 but without a lens interposed between the energy source and the water-bolus.
Figure 4:
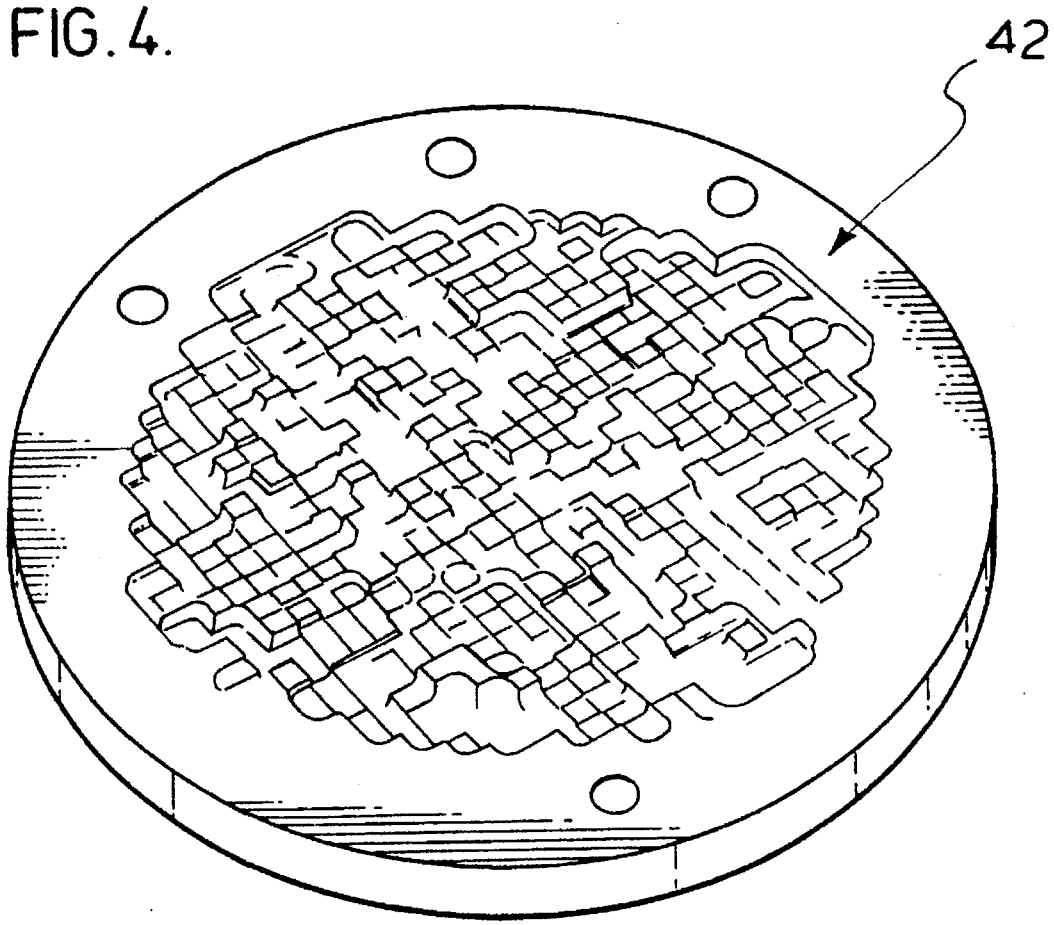
FIG. 4 is a perspective view of a field-conjugate lens of the invention of FIG. 1.

In a second embodiment as illustrated in FIG. 3, the system may be used without any focusing elements 36 (lenses) and the ultrasound energy applied directly to the skin and dermis layer with a water bolus interposed and achieve satisfactory and predictable subcutaneous adipose tissue temperatures in a work zone. In such a configuration, the ultrasound energy frequency, and the temperature-controlled water bolus temperature, become critical to each specific anatomical area (i.e. amount of subcutaneous fat and muscle, and proximity of large bones). Since ultrasonic energy tissue intensity is highest at the surface and decays exponentially with increasing tissue absorption and depth, if one controls the skin surface temperature at for example 36.5° C., the resultant sonically heated tissue temperature heating zone is shifted deeper into the tissue.

In clinical use, the ultrasonic energy source is applied to the local anatomical surface overlying the fat target. Ultrasonic energy is focused on the work zone through a field conjugate lens, (or without any lenses as illustrated in FIG. 3) through an interface element. The skin may at the operator's discretion, have topical lipolytic augmentation agents 48 applied to the skin as part of the acoustic interface (applicator gel), or separately, to magnify the planned temperature effect. The topically applied augmentation agents 48 penetrate into the deeper tissues and work zone by both passive diffusion, and by the process of ultrasonic-induced phonophoresis. The incident energy supplied by the transducer and focused by the focusing element is absorbed by fat cells at the work zone, as is the lipolytic augmentation agents 48. The absorbed energy increases the temperature of the adipose tissue located at the work zone. The surrounding tissue should not be heated substantially because of the very precise temperature field created by the conjugate acoustic lens when employed, or due to exponential decay depending on preselected operating parameters as has been described. The adipose tissue is heated to a temperature of about 40° C.–41.5° C., but no greater than 42° C., and maintained at such temperature for up to 20–25 minutes.

By maintaining the elevated temperature for an effective time, the rate of lipolysis of the fat tissue in the work zone is increased. This rate increase is proportional to the temperature differential above normal body tissue temperature which is generally lower than core body temperature depending on the specific anatomical region. For example, abdominal subcutaneous fat (not deep visceral) might be at a slightly higher temperature than the thigh subcutaneous tissue, and both would be lower than rectal temperature. At 41° C., for example, rates of up to 2.5 to 3 times normal body temperature lipolysis rates can be expected. Additionally, absorption of some lipolytic augmentation agent 48 by the work zone fat tissues independent of the above-mentioned temperature effect accelerates the normal adipose tissue lipolysis rate by an additional factor of 2 or 3 times. Taken together, a significant increase in lipolysis rate occurs in the fat tissue at the work zone.

By varying the focal point or work zone shallower, or deeper, and laterally and in a planned schedule of application, adipose tissue is progressively reduced in volume both in position and extent. This sustained increase in lipolysis rate, during a treatment encounter, and as part of an overall treatment program, achieves gradual and gentle volume reduction of target fat tissue at specific anatomical sites of choice without tissue trauma or destruction.

In an alternate embodiment, a radio frequency energy source is applied to transducer 34. Radio frequency energy is supplied by capacitive coupling directly to the skin for areas close to the dermal tissue via contact electrodes. Radio frequency induction focusing uses a plurality of focusing coils which are additive at the zone of interest and are subtractive elsewhere. Alternatively, the radio frequency energy may be focused by having a multiple beam phased array as it is per se well known. For concave focusing see, for example, "Tumour Reduction by RadioFrequency Therapy Response in 21 Patients", H. H. LeVeen, et al., JAMA, Vol. 235 at 2198–2200. Alternative radio frequency focusing constructions are disclosed in "Equipment For Local Hyperthermia Therapy of Cancer", C. F. Babbs, et al., Medical Instrumentation, Vol. 16, No. 5, September–October, 1982 at 245–248.

The disclosures of each of references noted herein are, including Gooberman, Cheung et al., LeVeen et al., and Babbs et al. are hereby incorporated herein by reference.

The above described arrangements are merely illustrative of the principles of the present invention. Other modifications and adaptions may occur to those skilled in the art, without departing from the spirit and scope of the present invention.

I claim:

1. A method of reducing adipose cell volume in a human patient by non-invasively, non-destructively, and atraumatically increasing a lipolysis rate at specific accumulations of subcutaneous adipose tissue, comprising the steps of:

selecting a desired work site in the patient's subcutaneous adipose tissue layer containing healthy adipose cells to be reduced in volume;

focusing radiant energy on said work site to raise the temperature thereof to between 40.0° to 41.5° C.; and maintaining the radiant energy focused on said work site to increase the lipolysis rate thereof sufficiently to cause release of free fatty acids, thereby reducing the volume of the adipose cells.

2. A method as claimed in claim 1, wherein said method includes a preliminary step of determining a schedule of treatment for said patient.

3. A method as claimed in claim 1 wherein said method includes an initial step of:

identifying a number of work sites for body contour modification by assessing overall health, fitness, and suitability of the patient for any local or general medical intervention and by performing baseline medical, laboratory, biometric, and contour measurements; said selecting step includes selecting one of the work sites as the desired work site, determining whether to utilize topical lipolytic augmentation agents at said desired work site in conjunction with radiant energy modalities, including ultrasonic, radio frequency and microwave, and selecting and applying a topical lipolytic agent to said work site prior to said focusing step and selecting a conjunctive source of said radiant energy;

determining an overall treatment program and schedule by projecting a number of encounters necessary to achieve satisfactory site-specific body contour modification by the reduction of local subcutaneous adipose tissue volume at said desired work site, and establishing a medical management program which achieves a calorie negative metabolic state.

4. A method as claimed in claim 1, wherein said method further comprises the step of employing an imaging apparatus for viewing the changes in volume of the adipose cells.

5. A method as claimed in claim 1, including supplying said radiant energy from an ultrasonic source.

6. A method as claimed in claim 1, including supplying said radiant energy from a radio frequency source.

7. A method as claimed in claim 1, including supplying said radiant energy from a microwave source.

8. A method as claimed in claim 1, including focusing said radiant energy on the work site using a field-conjugate acoustic lens having a configuration specific for the work site.

9. A method as claimed in claim 1, including focusing said radiant energy on the work site using a combination of a concave lens and a field-conjugate acoustic lens, wherein the field-conjugate acoustic lens has a configuration specific for the work site.

10. A method as claimed in claim 1, including directing said radiant energy on the work site through a temperature-controlled water bolus, thereby maintaining a predetermined temperature at a skin surface directly over the work site.

11. A method as claimed in claim 10, including controlling said focussing of radiant energy on the work site by controlling the temperature of the water bolus.

12. A method as claimed in claim 1, wherein said method further includes topically applying at least one adipose tissue lipolysis augmentation agent to a skin surface directly over the work site to enhance the local radiant energy effects.

13. The method as claimed in claim 12, including directing said adipose tissue lipolysis augmentation agent on said work site by phonophoresis.

14. A method as claimed in claim 1, including heating said work site with said radiant energy for up to 29 minutes.

15. A method as claimed in claim 1, including heating said work site with said radiant energy for between 20 and 29 minutes.

16. A method of reducing adipose cell volume in a human patient by non-invasively, non-destructively, and atraumatically increasing a lipolysis rate at specific accumulations of subcutaneous adipose tissue, comprising the steps of:

determining a schedule of treatment and identifying a number of work sites for body contour modification for said patient by assessing overall health, fitness, and suitability of the patient for any local or general medical intervention and by performing baseline medical, laboratory, biometric, and contour measurements; determining whether to utilize topical lipolytic augmentation agents in conjunction with radiant energy modalities, including ultrasonic, radio frequency and microwave; selecting a topical lipolysis augmentation agent and a conjunctive source of a radiant energy; determining an overall treatment program and schedule by projecting a number of encounters necessary to achieve satisfactory site-specific body contour modification by a reduction of local subcutaneous adipose tissue volume, and establishing a medical management program which achieves a calorie negative metabolic state;

selecting a desired work site from said number of work sites in the patient's subcutaneous adipose tissue layer containing healthy adipose cells to be reduced in volume;

topically applying said lipolysis augmentation agent to a skin surface directly over the work site;

focusing said radiant energy through conjugate field lenses of a specific configuration adapted for said work site and through a temperature-controlled water bolus, said radiant energy focusing on subcutaneous adipose tissues in said work site to raise the temperature thereof to between 40.0° to 41.5° C. said water bolus maintaining the skin surface at the work site at a predetermined temperature; and maintaining the radiant energy focused on said work site for up to 29 minutes, increasing said lipolysis rate thereof sufficiently to cause release of free fatty acids, thereby reducing the volume of the adipose cells;

employing an imaging apparatus for viewing the changes in volume of the adipose cells.

17. A method as claimed in claim 16, including supplying said radiant energy from an ultrasonic source.

18. A method as claimed in claim 16, including supplying said radiant energy from a radio frequency source.

19. A method as claimed in claim 16, including supplying said radiant energy from a microwave source.

20. The method as claimed in claim 16, including directing said adipose tissue lipolysis augmentation agent on said work site by phonophoresis.

* * * * *